United States Patent
Amoah et al.

(10) Patent No.: US 9,925,372 B2
(45) Date of Patent: Mar. 27, 2018

(54) REDUCTION OR REMOVAL OF PARTICLES WITHIN AN ENCLOSED CORPOREAL ATMOSPHERE

(75) Inventors: Francis Amoah, Reading (GB); Dominic Griffiths, Vale of Glamorgan (GB)

(73) Assignee: ASALUS MEDICAL INSTRUMENTS LIMITED, Cardiff (GB)

(*) Notice: Subject to any disclaimer, the term of this patent is extended or adjusted under 35 U.S.C. 154(b) by 990 days.

(21) Appl. No.: 14/348,340

(22) PCT Filed: Sep. 5, 2012

(86) PCT No.: PCT/GB2012/052172
§ 371 (c)(1),
(2), (4) Date: Mar. 28, 2014

(87) PCT Pub. No.: WO2013/045886
PCT Pub. Date: Apr. 4, 2013

(65) Prior Publication Data
US 2014/0228836 A1   Aug. 14, 2014

(30) Foreign Application Priority Data

Sep. 30, 2011 (GB) .................................. 1116889.5

(51) Int. Cl.
  *B03C 3/41*   (2006.01)
  *A61N 1/20*   (2006.01)
  (Continued)

(52) U.S. Cl.
  CPC .............. *A61N 1/325* (2013.01); *A61B 18/00* (2013.01); *A61B 18/04* (2013.01); *B03C 3/40* (2013.01);
  (Continued)

(58) Field of Classification Search
  CPC ....... B03C 3/383; B03C 3/41; B03C 2201/10; B03C 2201/26; A61N 1/20; A61B 18/00;
  (Continued)

(56) References Cited

U.S. PATENT DOCUMENTS 6,379,427 B1   4/2002   Siess
6,919,053 B2   7/2005   Joannou
(Continued)

FOREIGN PATENT DOCUMENTS

WO   2011010148 A2   1/2011

*Primary Examiner* — Christopher P Jones
*Assistant Examiner* — Minh-Chau Pham
(74) *Attorney, Agent, or Firm* — King & Schickli, PLLC

(57) ABSTRACT

Apparatus (100) and method are disclosed for removing or reducing the number of particles in an enclosed atmosphere during intracorporeal procedures. The apparatus comprises a housing (180) adapted to be placed against the body on which a procedure is to be formed, a first electrode (140) external to the housing for contacting the body, an elongated electrically insulated probe (130) extending from the housing (180) and being insertable into an intracorporeal body cavity (C) in which a procedure is to be performed, a second electrode (150) at the free end of the probe, and circuit means (110) for generating voltage between said first and second electrodes. The method comprises applying a voltage between the electrodes sufficient to cause local ionization of particles within the body cavity such that they migrate away from the second electrode, thereby removing or reducing the number of particles generated during the procedure from the enclosed atmosphere at or around the site of the procedure.

17 Claims, 3 Drawing Sheets

(51) Int. Cl.
*A61B 18/00* (2006.01)
*A61B 18/02* (2006.01)
*A61B 18/20* (2006.01)
*A61N 1/32* (2006.01)
*B03C 3/40* (2006.01)
*A61B 18/04* (2006.01)

(52) U.S. Cl.
CPC ..... *A61B 2218/008* (2013.01); *B03C 2201/26* (2013.01)

(58) Field of Classification Search
CPC ............ A61B 17/320068; A61B 18/02; A61B 18/1445; A61B 18/20; A61B 2018/00083; A61B 2018/1497; A61B 2218/008
USPC ................... 55/385.1; 95/55; 96/80; 604/28
See application file for complete search history.

(56) References Cited

U.S. PATENT DOCUMENTS

| | | |
|---|---|---|
| 2003/0147784 A1 | 8/2003 | Joannou |
| 2010/0018398 A1 | 1/2010 | Krell |
| 2012/0067212 A1* | 3/2012 | Warren ................. A61B 18/00 95/57 |

\* cited by examiner

REDUCTION OR REMOVAL OF PARTICLES WITHIN AN ENCLOSED CORPOREAL ATMOSPHERE

FIELD OF THE INVENTION

This invention relates to the reduction or removal of particles, such as smoke particles, that are generated during intracorporeal procedures such as medical or cosmetic procedures on the human body.

In this specification the word "particles" is intended to include smoke, smoke particles, droplets or other matter suspended in a local atmosphere in which a procedure is to be performed, either before, during or after the procedure.

BACKGROUND OF THE INVENTION

It is well known that particles generated during procedures such as surgical procedures as a result of cutting flesh or cauterising wounds obscure the view of the person performing the procedure and may be hazardous to the health of surgical staff. In a general sense, particle removal methods, such as smoke removal methods usually comprise means by which the smoke is physically removed by e.g. a vacuum and then vented externally of the operating theatre, or by filtering out the smoke particles and re-circulating air. However, in practice this may not be feasible or may be only partially achieved, meaning that health is at risk for those participating in the procedure and, more directly, the person carrying out the procedure can be hampered by the poor visibility caused by the presence of unwanted particles in the enclosed atmosphere, which may typically be an artificially inflated area of a patients body, such as during laparoscopic procedures where a suitably inert gas such as $CO_2$ is introduced into the patient via an access port to inflate the area of the patients body where the procedure is to be carried out prior to the procedure commencing.

Even where cryosurgery is employed, frozen vapour, water droplets or other matter can be generated which singly or collectively act like a fog suspended in the local atmosphere, which again can obscure the view of those involved in the procedure. In WO 2011/010148 apparatus and methods are described for the removal or reduction of particles in an enclosed atmosphere which employ a high voltage to ionise particles and thereby remove them, partially or wholly, from the site of the procedure being undertaken and the present invention is derived from the realisation that this technique can be improved further by simplifying the process by which e.g. patients undergoing surgery can be prepared in a manner by which the time taken to perform the required procedure is kept to a minimum.

SUMMARY OF THE INVENTION

According to a first aspect of the invention there is provided an apparatus for removing or reducing the number of particles in an enclosed atmosphere during intracorporeal procedures, the apparatus comprising or including a housing adapted to be placed against the body on which a procedure is to be formed, such as a medical or cosmetic procedure, a first electrode external to the housing for contacting the body, an elongated electrically insulated probe extending from the housing and being insertable into an intracorporeal body cavity in which a procedure is to be performed, and a second electrode at the free end of the probe, and circuit means for generating voltage between said first and second electrodes sufficient to cause local ionisation of particles within the body cavity such that they migrate away from the second, electron discharge, electrode, thereby removing or reducing the number of particles generated during the procedure from the enclosed atmosphere at or around the site of the procedure.

With this arrangement, the apparatus can be substantially portable and hence largely self contained, such as being battery operable, in which certain parts of the apparatus, such as the probe and the second electrode, may be replaceable, such as being disposable, so that the same apparatus can be safely used with different patients without raising the potential for cross-contamination. As such the device is constructed in such a way as to allow it to undergo repeated sterilisation cycles in order to guarantee sterility between uses. The invention therefore lends itself to include a housing in which the first electrode, which may conveniently be annular or some other suitable shape, is adapted to be placed onto the skin of a patient adjacent an area beneath the skin where an intracorporeal procedure is to be performed, and with the probe itself conveniently extending from the axis of the annulus so that it can be inserted within an aperture in and through the skin of the patient to emerge within an artificially inflated local atmosphere within the patient's body around the site where the procedure is to be performed, the length of the probe being conveniently adjustable or of a chosen length whereby the second electrode is not thereafter in direct contact with any part of the patient's body. As a consequence, ionised particles in the enclosed atmosphere will thereafter migrate away from the second electrode continuously as the procedure is being performed, thereby ensuring or at least improving best visibility for the person carrying out the procedure.

Although the means for generating ionising voltage is conveniently within the housing it may instead be generated remote therefrom and, instead of being battery powered, may be powered from mains electricity.

The second electrode may be of any convenient shape but, in particular, it may be brush-like, to provide a relatively large surface area for improving the ionisation of particles in the immediately surrounding area.

The second electrode may alternatively be formed from any filament-type structure.

The circuit means for generating voltage between the first and second electrodes sufficient to cause local ionisation of particles within the body cavity may provide a voltage up to about 30 KV, but preferably between 5 KV and 15 KV.

Where the circuit means is powered by a rechargeable battery the battery may be recharged directly through contact with electrical conductors or indirectly by electromagnetic induction.

The apparatus may further include an introducer tool, such as a tapered solid needle generally of diameter less than that of a catheter, which may therefore be mounted thereon from the sharp end but greater than the diameter of the probe and attendant second electrode such that the needle can be used to introduce the catheter into the body cavity of the patient and then removed. The probe is secured in the catheter in such as way as to provide an air-tight seal thereby preventing unintentional loss of the gas used to inflate the cavity.

In accordance with a second aspect of the invention there is provided a method of removing or reducing the number of particles in an enclosed atmosphere during intracorporeal procedures, the method including the steps of, in any required order, providing an apparatus according to the first aspect of the invention and variations thereof and placing it against a body on which an intracorporeal procedure is to performed such that the first electrode is electrically connected to the body, inserting the second electrode into the enclosed atmosphere and thereafter ionising particles therewithin such that they migrate away from the second electrode to thereby permit the procedure to be performed with a total or a reduced number of particles being visible. The ionisation is most preferably created by a negative corona although in principle a positive corona may also be used but will result in a lower efficiency of particulate clearing.

BRIEF DESCRIPTION OF THE DRAWING FIGURES

The invention may be performed in various ways and an embodiment thereof will now be described, by way of example only, reference being made to the accompanying drawings, in which:

FIG. 5 shows a catheter introducer tool suitable for use with the probe catheter of FIG. 6; and FIG. 6 shows a probe catheter for use with the introducer tool of FIG. 5.

DETAILED DESCRIPTION OF THE INVENTION

Figure 1:
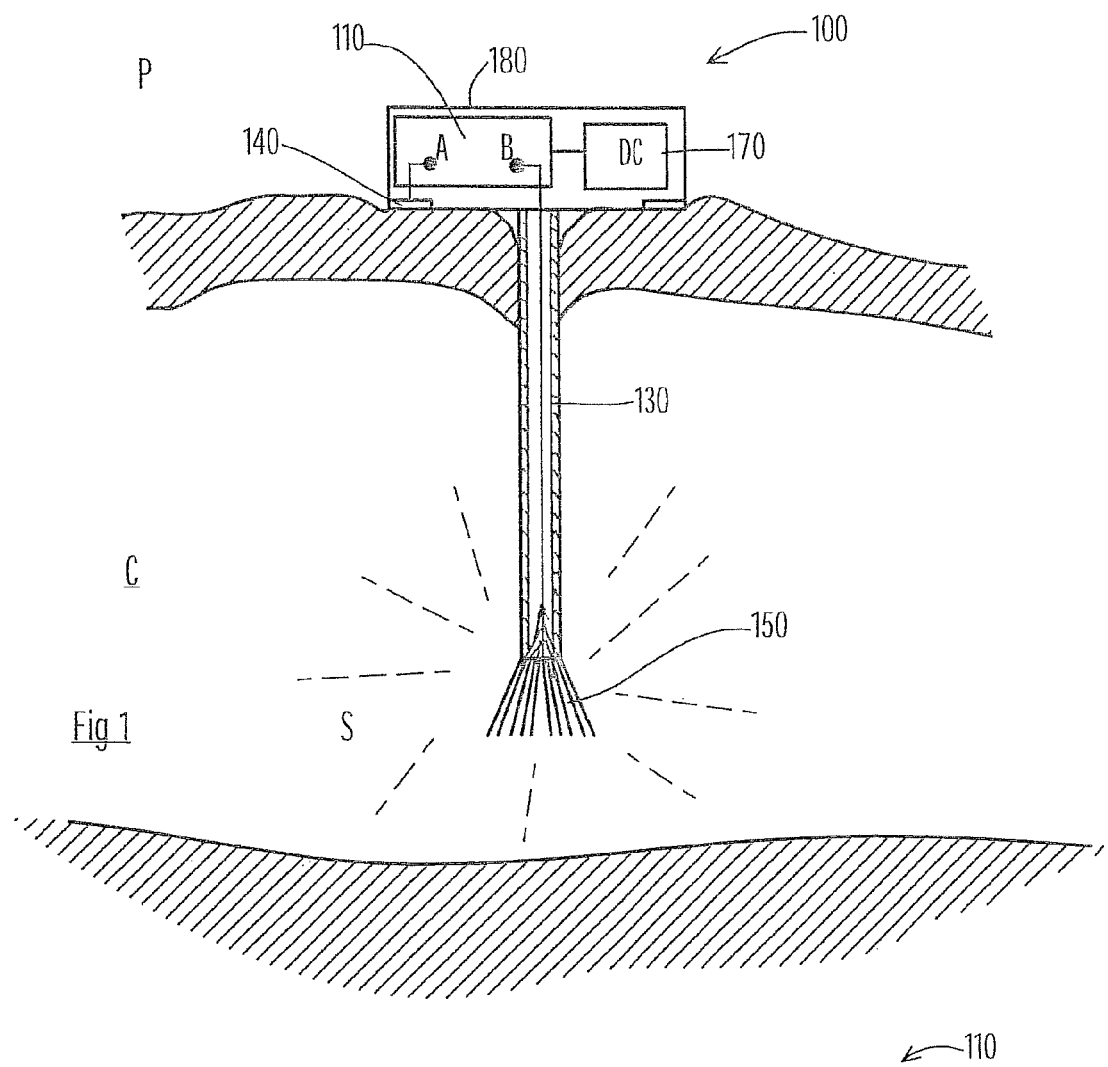
FIG. 1 shows a schematic representation of apparatus according to the invention in use.

Referring firstly to FIG. 1, there is shown particle removal apparatus 100 which is used to remove smoke particles S from the site of a body cavity C of the patient P, during, for example, intracorporeal surgical procedures at that site. The apparatus 100 having a cylindrical housing 180 containing a high voltage circuit 110 having poles A, B driven by a DC power source 170 in the form of a rechargeable battery, although the power source may instead be a non-rechargeable battery or even take the form of a transformer and associated DC rectifier connected or connectable to mains electricity.

On the underside of the housing 180 is a first electrode 140, being annular and, in the position shown, is resting on the outer skin of the patient P, where, in practice, an electrically conductive gel may be applied to the patient or the first electrode 140 in order to improve conductance therebetween.

Extending centrally downwards from the housing 180 is a tubular insulated probe 130 on the free end of which is a brush-like second electrode 150 electrically connected to pole B of the circuit 110.

Figure 2:
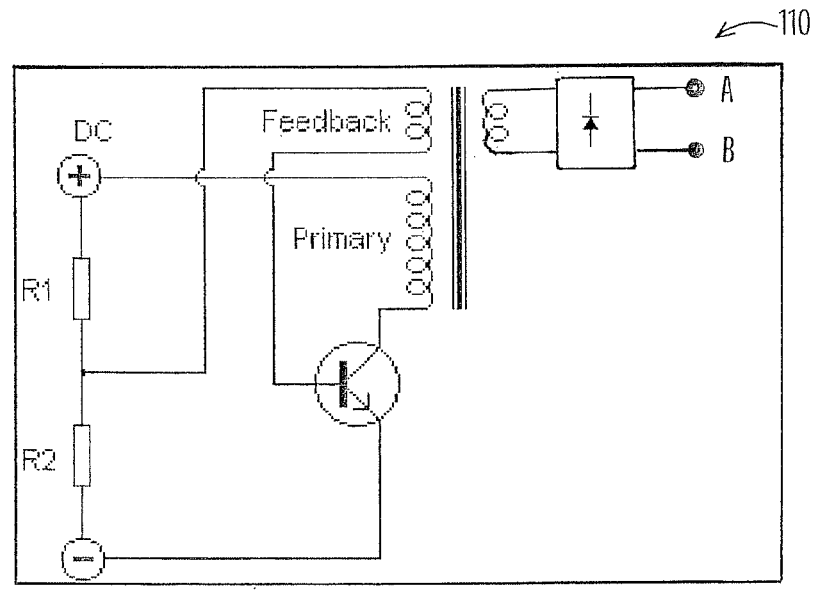
FIG. 2 shows a simple circuit for powering the apparatus shown in FIG. 1.

Referring now to FIG. 2 there is shown a simple high voltage circuit for powering the particle removal apparatus 100 and in which a low voltage DC source is used to step up the voltage to a required higher voltage between the poles A and B sufficient to cause a high voltage, low current, electric field to exist between the first electrode 140 via its contact with the patient P and the second electrode 150, thereby causing ionisation of particles in that region such that they migrate away from the second electrode 150. These particles can collect on the body surfaces, to be later removed once the procedure is complete.

Figure 3:
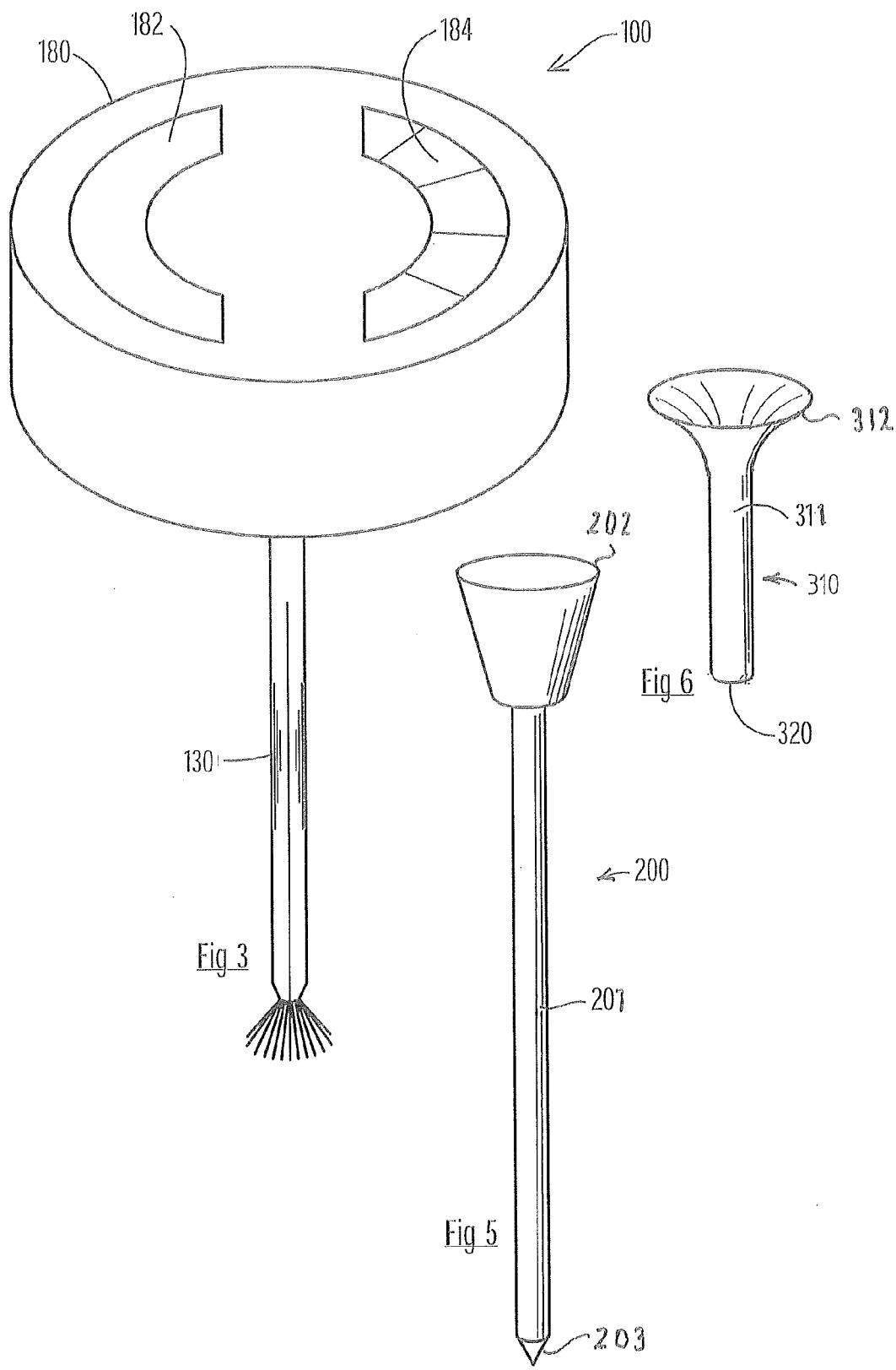
FIG. 3 shows a perspective view of the apparatus shown in FIG. 1 in more detail.
Figure 4:
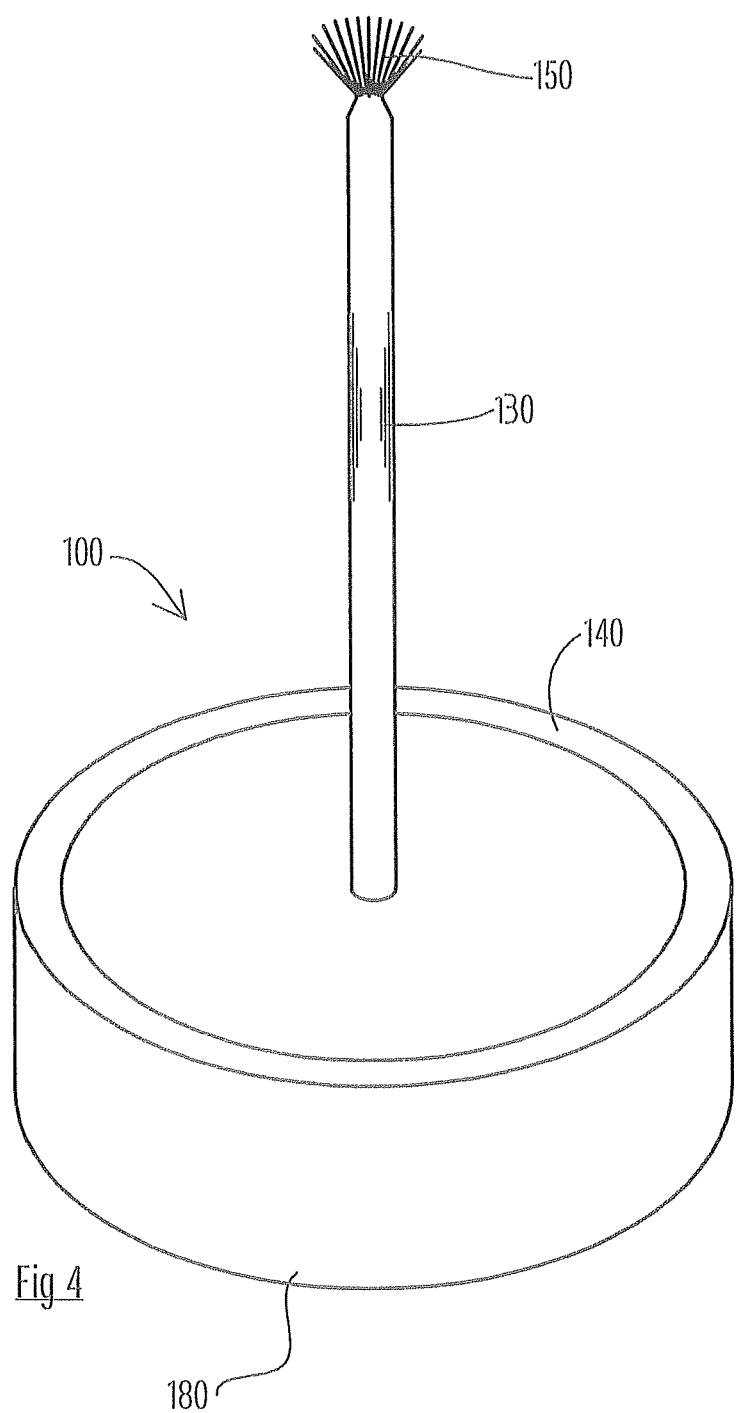
FIG. 4 shows an underneath view of the apparatus shown in FIG. 3.

FIGS. 3 and 4 show respective upper and lower perspective views of the apparatus 100. In FIG. 3 the upper surface of the housing 180 includes an arcuate display 182 for displaying the status of the apparatus including, for example, the charge state of the battery 170 and the functioning of the high voltage circuit 110. Opposite to the display 180 is a set of controls 184 for turning the device on and off and for testing it as required.

FIG. 4 shows how the annular first electrode 140 is positioned around the perimeter of the underside of the housing 180 and also shows the second electrode 150 which, by virtue of being brush-like, provides a relatively large surface area for improving the ionisation of particles between the first and second electrodes 140, 150 via the body of the patient P so that the enclosed atmosphere in the cavity C can be kept substantially particle-free in a manner to be described.

FIG. 5 shows a probe catheter introducer tool 200 in the form of a needle having a solid stem 201, a finger grip 202 at one end and a sharp point 203 at the other. The probe catheter 310 shown in FIG. 6 has a tubular stem portion 311, a funnel-shaped upper end 312 and a blunt lower end 320.

With this arrangement, the catheter 310 can be mounted on the introducer tool 200 which is then used to pierce an outer wall, such as an abdominal wall, of the patient P, whereafter the tool 200 can be removed leaving the catheter 310 in place to receive the free end of the probe 130 and hence the second electrode 150 via the funnel 312, the probe 130 and the second electrode 150 then emerging within the body cavity C from the lower end 320 of the catheter 310.

The outer diameter of the introducer tool and/or catheter is preferably small, i.e. less than 5 mm to avoid the need for post-operative sutures when it has been removed. The outer surface of the probe 130 is preferably sealable (for example by a tight interference fit at some point along its length, via an o-ring seal, a lever lock or other similar means), against the inner surface of the catheter to form a substantially air tight seal to prevent or inhibit gas from escaping from the inflated body cavity.

The catheter length and/or the probe length is preferably adjustable and depth indicators may be provided so that users can gauge how far into the body the probe has been inserted. The depth indicators are preferably visible on the exterior of the probe 130 so that its depth can be ascertained using a surgical visualisation instrument such as a laparoscope or endoscope during the surgical procedure.

A catheter clasp may also be provided for locking the probe in relation to the catheter so that depth/position of the probe can be temporarily fixed. The catheter clasp can also be fixable to the patients body such that the probe depth and/or position is fixable relative to the patient's body.

One embodiment of the invention only has been described and illustrated, and it will be readily apparent that other embodiments, modifications, additions and omissions are possible within the scope of the invention.

Although the battery 170 has been shown housed within the housing 180, it will be appreciated that a means of powering the circuit 110 could be provided elsewhere. The battery 170 may be removable from the housing 180. In a modification, the battery 170 may be charged via inductive link such that the apparatus 100 can be placed in a cradle and recharged without the need for exposed recharging terminals, which could otherwise present a health risk. The apparatus 100 may be a disposable item, in which case rechargeable batteries need not be used. Capacitive type electrical storage could also be used instead of, or as well as, battery electrical storage.

Other refinements are possible within the scope of the claims. For example, it is envisaged that the high voltage generating source would be insulated from the outside world and only the two electrodes mentioned above would be externally accessible. This allows for safer operation of the device and reduces the chances of electric shock. The embodiment described in the present application describes the second electrode 150 as being mounted directly to the housing 180 upon which the first electrode 140 is also attached. However, it will be appreciated that such mounting of the second electrode 150 may be detachable from the housing 180 rather than being permanently fixed to it and this may be achieved using a suitable electrical connector and insulated receptacle for use with the second electrode. Furthermore, a short electrical cable may be deployed to allow the surgeon to place the housing 180 and the first electrode 140 a short distance away from the site of insertion of the second electrode 150, but still within the sterile surgical field.

The brush-like second electrode 150 has "bristle" elements which are each of a size that has been carefully chosen since metal bristles over a thickness of around 100 microns can act like needles and consequently may puncture internal organs if used within a body cavity. Likewise bristles having a thickness of less than about 50 microns tend to be too weak so bristles of around 75 microns are about ideal. However, bristles between 10 and 100 microns can be satisfactory. It has been found that the number of bristles does not greatly affect the rate of smoke clearing with as few as ten bristles performing satisfactorily. However for a useful, robust, and efficient electrode, bristles of around the size mentioned above and around 40 in number are employed. The bristles have been found to work well when manufactured from medical grade stainless steel, although other materials may be suitable.

The apparatus and method of the invention may be varied according to requirements, having as its ultimate objective the removal or reduction of e.g. smoke particles at the site of a patient undergoing a medical or cosmetic procedure whereby the person performing the procedure is afforded better visibility therefor as a result of fewer particles being present in that region than would be the case without the apparatus and method of the invention.

This Patent application is intended to be interpreted in the light of WO2011/010148, the disclosures of which are intended to be incorporated herein by reference.

The invention claimed is:

1. An apparatus (100) for removing or reducing the number of particles in an enclosed atmosphere during intracorporeal procedures, the apparatus comprising or including:
   a housing (180),
   a first electrode (140) external to the housing arranged on the underside of the housing, adapted to be placed on the skin of a patient on which a procedure is to be performed,
   an elongated electrically insulated probe (130) extending downwards from the housing so that it can be inserted within an aperture in and through the skin of the patient and to emerge within an intracorporeal body cavity (C) in which the procedure is to be performed,
   a detachable second electrode (150) at the free end of the probe, said second electrode mountable via an electrical connector to an insulated receptacle for use with the second electrode, and
   a circuit (110) for generating voltage between said first and second electrodes sufficient to cause local ionisation of particles within the body cavity such that they migrate away from the second electrode, thereby removing or reducing the number of particles generated during the procedure from the enclosed atmosphere at or around the site of the procedure.

2. Apparatus according to claim 1, wherein the first electrode is adapted to be placed onto the skin of a patient adjacent an area beneath the skin where an intracorporeal procedure is to be performed.

3. Apparatus according to claim 1, wherein, the first electrode comprises a substantially annular shape.

4. Apparatus according to claim 3, wherein the probe is arranged to extend from an axis of the annular shaped first electrode.

5. Apparatus according to claim 1, wherein the length of the probe is adjustable.

6. Apparatus according to claim 1, wherein the circuit is disposed within the housing.

7. Apparatus according to claim 1, wherein the circuit is disposed remote from the housing.

8. Apparatus according to claim 1, wherein the second electrode comprises a substantially brush-like shape.

9. Apparatus according to claim 1, wherein the second electrode comprises a filament-type structure.

10. Apparatus according claim 1, wherein the circuit is arranged to provide a voltage up to about 30 KV.

11. Apparatus according to claim 1, wherein the circuit is arranged to provide a voltage in the range between 5 KV and 15 KV.

12. Apparatus according to claim 1, wherein the circuit is powered by a rechargeable battery (170) which may be recharged directly through contact with electrical conductors or indirectly by electro-magnetic induction.

13. Apparatus according to claim 1, wherein the circuit is powered by a mains power supply, via transformer and direct current rectifier.

14. Apparatus according to claim 1, further comprising an introducer tool (200), for introducing a catheter (310) into the body cavity of the patient.

15. Apparatus according to claim 14, wherein the probe is securable in the catheter to provide an air-tight seal.

16. A method of removing or reducing the number of particles in an enclosed atmosphere during intracorporeal procedures, the method including the steps of, in any required order:
   providing an apparatus (100) according to claim 1,
   placing the apparatus against a patient on which an intracorporeal procedure is to be performed such that the first electrode (140) is electrically connected to the skin of the patient,
   inserting the second electrode (150) into the enclosed atmosphere, and
   ionising particles within the atmosphere such that they migrate away from the second electrode to thereby permit the procedure to be performed with a total or a reduced number of particles being visible.

17. A method according to claim 16, wherein the ionisation is created by a negative corona.

* * * * *